United States Patent
Majeed et al.

(10) Patent No.: US 11,045,517 B2
(45) Date of Patent: Jun. 29, 2021

(54) COMPOSITION FOR THERAPEUTIC MANAGEMENT OF HYPOMELANOTIC SKIN CONDITIONS

(71) Applicants: Muhammed Majeed, Bangalore (IN); Kalyanam Nagabhushanam, East Windsor, NJ (US); Prasad M Peethambaran, Bangalore (IN); Lakshmi Mundkur, Bangalore (IN)

(72) Inventors: Muhammed Majeed, Bangalore (IN); Kalyanam Nagabhushanam, East Windsor, NJ (US); Prasad M Peethambaran, Bangalore (IN); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/785,670

(22) Filed: Feb. 10, 2020

(65) Prior Publication Data
US 2020/0276257 A1    Sep. 3, 2020

(51) Int. Cl.
| | | |
|---|---|---|
| *A61K 36/00* | (2006.01) | |
| *A61K 36/67* | (2006.01) | |
| *A61K 36/71* | (2006.01) | |
| *A61P 17/00* | (2006.01) | |
| *A61K 9/06* | (2006.01) | |
| *A61K 9/107* | (2006.01) | |
| *A61K 36/53* | (2006.01) | |

(52) U.S. Cl.
CPC ............ *A61K 36/67* (2013.01); *A61K 9/06* (2013.01); *A61K 9/107* (2013.01); *A61K 36/53* (2013.01); *A61K 36/71* (2013.01); *A61P 17/00* (2018.01)

(58) Field of Classification Search
CPC ....................................................... A61K 36/00
USPC ............................................................ 424/725
See application file for complete search history.

(56) References Cited

PUBLICATIONS

Kumar et al., Pestology (2011), 35(2), 43-45 CODEN: PSTOEQ; ISSN: 0970-3012.*

* cited by examiner

*Primary Examiner* — Michael V Meller

(57) ABSTRACT

The present invention discloses a composition comprising *Nigella sativa* extract standardized to contain not less than 0.1% w/w thymoquinone and not less than 0.01% w/w thymohydroquinone, *Coleus forskolii* extract standardized to contain not less than 90% w/w forskolin and *Piper nigrum* extract standardized to contain not less than 95% w/w piperine extract for use in enhancing melanogenesis in mammalian cells. The invention also discloses the use of above mentioned composition in the therapeutic management of hypomelanotic skin conditions and in reducing the progression of depigmentation of skin in vitiligo in mammalian skin.

1 Claim, No Drawings

COMPOSITION FOR THERAPEUTIC MANAGEMENT OF HYPOMELANOTIC SKIN CONDITIONS

CROSS REFERENCE TO THE RELATED APPLICATIONS

This is a US conventional application claiming priority from the Indian provisional patent application number 201941005316 filed on Feb. 11, 2019

FIELD OF INVENTION

The invention pertains compositions for the therapeutic management of hypomelanotic conditions. The invention further relates to a composition comprising *Nigella sativa* extract, *Piper nigrum* extract, and *Coleus forskolii* extract for the therapeutic management of hypomelanotic condition.

DESCRIPTION OF THE PRIOR ART

Hypomelanotic conditions are pigmentary disorders characterized by reduced melanin content in the skin resulting in white patches in the skin. There are numerous factors which cause hypomelanosis which include, autoimmune disorder, viral infection, hereditary, oxidative stress, neurological disorders, sun burns or exposure to harmful chemicals. Vitiligo is a condition wherein de pigmentation or loss of skin color is observed in patches. This mainly occurs due to the decrease in the production of melanin. Major symptoms of vitiligo involve discolored patches of irregular sizes and shapes on the skin. The patch is small initially and progresses to cover the entire skin in some cases.

The state-of-the-art treatment for vitiligo include phototherapy with UVB and UVA light wherein the affected area of the skin is exposed to UVB lamps. UVA treatments include administration of a drug (psoralen) that makes, the skin more sensitive to UV light. The duration of treatment is 2 or more years and the effects are slow as a result patient discontinue the treatment. Psoralen can increase the risk of sunburn skin damage and consequently skin cancer and therefore not recommended for long term use. Moreover, there are side effects associated with the drug administration like gastric discomfort, cutaneous photosensitivity reaction, sunburn, burning, itching, nausea, tanning and painful erythma. Stressful life and other factors like clothes, smoking habit also affect the treatment negatively (Lakhani and Despande (2014) "Various Treatments for Vitiligo: Problems Associated and Solutions" Journal of applied pharmaceutical science 4(11); 101-105). All these methods are non-reliable as the skin in vitiligo becomes much sensitive to the sun and other radiations. Prolong exposure of the skin to UV radiations also lead to cancer.

Other treatment modalities involve skin camouflages wherein cosmetic creams are used to camouflage the affected areas of the skin. However, the skin camouflage method is tedious and temporary. All the above-mentioned methods increase the patient's mental stress and social discomfort. Hence, there is an industrial need to find a safe and reliable alternative to control the discoloration or hypomelanotic condition. Since condition develops gradually and involves decrease in melanin synthesis, topical preparation that help in enhancing Melanogenesis might help in effectively managing the condition (Niu and Aisa (2017) "Upregulation of Melanogenesis and Tyrosinase Activity: Potential Agents for Vitiligo", Molecules. 22(8): 1303).

Numerous reports indicate the use of natural compounds for the management of vitiligo and related conditions. The herbal extracts of *Ginko biloba, Cucumis melo* (aka. Muskmelon) extract containing *Cucumis melo* superoxide dismutase (SOD), Green Tea. *Picrorhiza kurroa, Polypodium leucotomos, Amni visnaga, Capsaicin, Curcumin, Pyrostegia venusta* etc. have been used individually in treatment of vitiligo since ancient times (Gianfaldoni et al., (2018) "Herbal Compounds For The Treatment Of Vitiligo", Open Access Maced J Med Sci. 6(1): 203-207). The following prior art documents discloses use of herbal extracts for the treatment of vitiligo and related depigmentation conditions.

1. Chinese patent application number CN103169776A discloses composition containing herbal extracts of *Tribulus terrestris, Polygonum multiflorum,* parts of *Fructus psoraleae,* parts of *Dahurian angelica* root, parts of fig leaves and parts of (raw) licorice in treatment of Vitiligo.
2. Patent Application. KR 20110008610 describes a composition containing Cassia alata extract for treating vitiligo. The Casia alata extract is isolated using water, alcohol of C!C4 or mixture solvent thereof.
3. Patent KR101119966B1 describes an herbal composition comprising *Cryptanthus* as an active ingredient (vitiligo) medicament for treatment of vitiligo.
4. Patent application number U.S. Ser. No. 13/277,605 discloses a composition containing Sophora japonica extract as an active ingredient. Sophora japonica extract enhances melanin synthesis by increasing the activity of tyrosinase which is critical in intracellular melanin synthesis and promoting the expression of tyrosinase and TRP-2 mRNA.
5. Niu and Aisa (2017) "Upregulation of Melanogenesis and Tyrosinase Activity: Potential Agents for Vitiligo", Molecules. 22(8):1303), reviews the use of extracts and active ingredients of plants, on their effect in enhancing melanin synthesis and tyrosinase activity, for the design and development of novel anti-vitiligo agents.

However, a combination of ingredients which provide a synergistic effect in enhancing melanin synthesis is lacking. Black pepper or *Piper nigrum* also known as peppercorn belonging to family Piperaceae reduces the progressing de pigmentation in mammalian skin. *Nigella ativa* or Black cumin seed belonging to family Ranunculaceae have 47 volatile compounds wherein Thymoquinone (TQ), thymohydroquinone (THQ), as the major compounds. The volatile compounds in Nigella are proved to have anti-microbial, anti-fungal, anti-parasitic, wound healing and acne vulgaris. Indian coleus or *Coleus forskohlii* exhibits antibacterial activity and is also a cyclic adenosine monophosphate stimulator. Although all these extracts are individually reported to have some effects on the skin, a synergistic composition that is very effective in increasing the melanin content in the skin is lacking. The present invention solves the above-mentioned problem by disclosing a synergistic composition comprising *Nigella sativa* extract, *Coleus forskolii* extract and *Piper nigrum* extract, for managing the hypomelanotic conditions like vitiligo by enhancing melanin synthesis.

The principal objective of the invention is to disclose a composition comprising *Nigella sativa* extract, *Coleus forskolii* extract and *Piper nigrum* extract for use in enhancing melanogenesis in mammalian cells.

It is another objective of the invention to disclose a composition comprising *Nigella sativa* extract, *Coleus forskolii* extract and *Piper nigrum* extract for use in the therapeutic management and reducing the progression of depigmentation of skin in vitiligo by increasing melanin synthesis.

The present invention fulfils the aforesaid objectives and provides further related advantages.

SUMMARY OF THE INVENTION

In a most preferred embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine extract for use in enhancing the synthesis of melanin in mammalian cells.

In another preferred embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine for use in the therapeutic management of hypomelanotic skin conditions in mammals.

In yet another preferred embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine, for use in reducing the progression of depigmentation of skin in vitiligo and associated conditions in mammals.

Other features and advantages of the present invention will become apparent from the following more detailed description, which illustrate, by way of example, the principle of the invention.

DETAILED DESCRIPTION OF THE EMBODIMENTS OF THE INVENTION

In a most preferred embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine. In a related aspect, the composition comprises of 10% w/w *Nigella sativa* extract standardized to contain not less than 0.1% w/w thymoquinone, not less than 0.01% w/w thymohydroquinone, 0.5% w/w *Coleus forskolii* extract standardized to contain not less than 90% w/w forskolin and 2% w/w *Piper nigrum* extract standardized to contain not less than 95% w/w piperine. In another related aspect, the aforesaid composition is used for enhancing melanin synthesis in mammalian cells. In another related aspect, the composition is used for the therapeutic management of hypomelanotic skin conditions. In yet another related embodiment, the composition is formulated using pharmaceutically/nutraceuticals acceptable excipients, adjutants, diluents or carriers and administered/applied topically on the affected areas in the form of creams, lotions, ointments, gel or emulsions.

In another most preferred embodiment, the invention discloses a method of enhancing melanin synthesis in mammalian cells, said method comprising step of bring into contact mammalian cells with a composition comprising 5-15% w/w *Nigella sativa* extract standardized to contain not less than 0.1% w/w thymoquinone and not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine, to bring about an increase in melanogenesis. In a related aspect, the increase in melanogenesis is effective in the therapeutic management of hypomelanotic skin conditions.

In another preferred embodiment the invention discloses a method of therapeutic management of hypomelanosis in mammals, said method comprising step of administering a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine, to mammals in need of such therapy, for effectively managing hypomelanosis by increasing melanogenesis. In a related aspect, the composition is formulated using pharmaceutically/nutraceuticals acceptable excipients, adjutants, diluents or carriers and administered/applied topically on the affected areas in the form of creams, lotions, ointments, gel, or emulsions. In another related aspect, the mammal is human.

In related embodiment, the invention discloses a method to reduce the progression of depigmentation of skin in vitiligo by increasing melanin synthesis, said method comprising step of administering a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine, to mammals in need of such reduction. In a related aspect, the composition is formulated using pharmaceutically/nutraceuticals acceptable excipients, adjutants, diluents or carriers and administered/applied topically on the affected areas in the form of creams, lotions, ointments, gel or emulsions. In another related aspect, the mammal is human.

In yet another preferred embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine extract for use in enhancing melanogenesis in mammalian cells. In a related aspect, the increase in melanin synthesis is effective in the therapeutic management of hypomelanotic skin conditions.

In a related embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine for use in the therapeutic management of hypomelanotic skin conditions in mammals. In a related aspect, the therapeutic effect of managing hypomelanotic skin conditions is by increasing melanin synthesis in the skin. In another related aspect, the composition is formulated using pharmaceutically/nutraceuticals acceptable excipients, adjutants, diluents or carriers and administered/applied topically on the affected areas in the form of creams, lotions, ointments, gel or emulsions. In yet another related aspect, the mammal is human.

In another related embodiment, the invention discloses a composition comprising 5-15% w/w *Nigella sativa* extract standardized to contain not less than 0.1% w/w thymoquinone, not less than 0.01% w/w thymohydroquinone, 0.1-1% w/w *Coleus forskolii* extract standardized to contain not less than 90% w/w forskolin and 1-2% w/w *Piper nigrum* extract standardized to contain not less than 95% w/w piperine, for use in reducing the progression of depigmentation of skin in vitiligo and associated conditions in mammals. In a related aspect, the reduction in depigmentation of skin is brought about by increasing melanin synthesis. In another related aspect, the composition is formulated using pharmaceutically/nutraceuticals acceptable excipients, adjutants, diluents or carriers and administered/applied topically on the affected areas in the form of creams, lotions, ointments, gel, or emulsions. In yet another related aspect, the mammal is human.

The following illustrative example further discloses the preferred embodiments of the invention:

Example 1: Melanogenic Activity of *Nigella sativa* Extract, *Coleus forskolii* Extract and *Piper nigrum* extract Plant Extracts The plants used in the preparation of the composition are *Nigella sativa, Piper nigrum,* and *Coleus forskolii.* The *Nigella sativa* extract is obtained and standardized using a Super Critical Fluid Extraction (SCFE) process as outlined in patent application no. US 2019-0192447. The *Piper nigrum* extract is obtained using a process outlined in U.S. Pat. No. 5,536,506. The *Coleus forskolii* extract is available from Sami Labs Limited, Bangalore, India and Sabinsa Corporation, NJ, USA, standardized to contain 95% forskolin. The extracts are mixed in the different ratios and tested at a concentration of 50 mg/ml:

Melanogenic Activity

Background and Object

In the epidermis, melanocytes synthesize melanin, which is responsible for skin pigmentation. Melanin synthesis is carried out by cell specific enzymatic pathway controlled by tyrosinase (EC 1.14.18.1), the enzyme that catalyzes the initial two rate-limiting reactions of this process, the hydroxylation of tyrosine to Dihydroxy phenyl alanine (dopa) and its subsequent oxidation to dopaquinone. Melanin is the natural pigment found in human skin, which absorbs and protects against the UV components of sunlight.

Melanin production (melanogenesis) is increased by exposure to sunlight, causing a darker skin color which is regarded as aesthetically pleasing by many humans. Disorders in melanogenesis lead to many skin diseases like vitiligo, a hypopigmentary disorder, and psoriasis, a hyperproliferative disorder of the keratinocytes. Affective enhancers of melanogenesis can be screened by the given assay.

Procedure

The required amount of the sample was weighed in 1 ml of solvent Di methyl Sulphoxide (DMSO) such that the DMSO concentration in the culture media is less than 0.5%. The main stock is then filtered using 0.22 μm syringe filter. Sample working concentrations were prepared in Dulbecco's Modified Eagle Medium (DMEM)—10% Fetal Bovine Serum media (FBS).

A culture flask with 80% confluent B16-F1 melanoma cell line from mouse was taken and the medium was discarded, and the cells were washed with 2 ml Phosphate Buffered Saline (PBS). Added 200 μl trypsin (10×) and 1.8 ml PBS to the flask and incubated for 5 min in $CO_2$ incubator after tapping gently. Neutralized the trypsin with 4 ml media (DMEM with 10% FBS) and centrifuged at 1200 rpm for 5 min and discarded the supernatant. Resuspended the pellet in 1 ml of medium and the cells were counted. Seeded $0.5 \times 10^4$ cells/well in 0.2 ml medium in 96 well plate for Melanin estimation and incubated the plate overnight at 37° C. in a $CO_2$ incubator in presence of 5% $CO_2$. The medium was changed with fresh medium containing 50 μg/ml concentration of the different ranges of the composition (0.2 ml/well) in duplicates. A control well was maintained in duplicates with only DMEM with 10% FBS media. The plated was incubated for 72 hrs in $CO_2$ incubator. After the incubation period, the supernatant was removed and to the cells 0.250 ml of 1N NaOH was added and heated at 100° C. for 1 hour. The absorbance was then read at 405 nm in a micro plate reader.

Calculation for Melanin Enhancement

The percentage of enhancement of melanin secretion is calculated using the formula;

%Melanin enhancement=(sample OD−Control OD)/Control OD*100

Where, OD is Optical Density

Results

The results are tabulated in table 1:

TABLE 1

% Melanin Enhancement using the composition.

| Sl. No. | *Nigella sativa* extract (%) | *Coleus forskolii* (%) | *Piper nigrum* extract (%) | Dose, μg/ml | Melanin Enhancement % |
|---|---|---|---|---|---|
| 1 | 10 | 0 | 0 | 50 | NIL |
| 2 | 0 | 0.5 | 0 | 50 | 41.2 |
| 3 | 0 | 0 | 1 | 50 | NIL |
| 4 | 0 | 0 | 2 | 50 | 5.7 |
| 5 | 10 | 0 | 2 | 50 | 14.5 |
| 6 | 10 | 0.5 | 0 | 50 | 53.4 |
| 7 | 10 | 0.5 | 1 | 50 | 56.5 |
| 8 | 10 | 0.5 | 2 | 50 | 62.1 |

The composition comprising *Nigella sativa* extract, *Coleus forskolii* extract and *Piper nigrum* extract at percentages of 10%, 0.5% and 2% respectively, showed a synergistic increase in melanogenesis. This was unexpected given that both *Nigella sativa* extract and *Piper nigrum* did not show any enhancement in melanogenesis at similar concentration.

Thus, the composition comprising *Nigella sativa* extract, *Coleus forskolii* extract and *Piper nigrum* extract can be used in formulation for the treatment of hypomelatonic conditions like vitiligo. The composition will be effective in reducing the condition and also in the preventing the progress of the condition in other areas of the skin.

Example 2: Formulations Containing *Nigella sativa* Extract, *Coleus forskolii* Extract and *Piper nigrum* Extract for Enhancement of Melanin Secretion in Hypomelanotic Skin Conditions The composition is formulated using pharmaceutically/nutraceuticals acceptable excipients, adjutants, diluents or carriers and administered/applied topically on the affected areas in the form of creams, lotions, ointments, gel or emulsions.

TABLE 2

Cream Formulation

| Active Ingredients |
| --- |
| 10% *Nigella sativa* extract, 95% forskolin and 2% *Piper nigrum* extract containing piperine |
| Other Ingredients/Excipients |
| Purified Water, Disodium EDTA, Cetostearyl Alcohol, Softemul 165 (INCI Name: PEG (100) Glycerol Stearate), Caprylic Capric Triglyceride, Tinogard TT (INCI Name: Pentaerythrityl Tetra-di-t-butyl Hydroxyhydrocinnamate), Phenoxyethanol Xiameter PMX 3031 (INCI Name: Cyclopentasiloxane (and) Phenyl Trimethicone (and) Dimethiconol (and) C12-15 Alkyl Benzoate (and) Dimethicone Crosspolymer), AMP 95 (INCI Name: Aminomethyl propanol), Propylene Glycol |

The above formulation is merely an illustrative example; any formulation containing the above active ingredient intended for the said purpose will be considered equivalent.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit, of the invention are intended to be included with the scope of the appended claims.

We claim:

1. A method of treating a human suffering from vitiligo consisting essentially of administering 5-15% w/w Nigella saliva extract, 0.1%-1% w/w Coleus forskolii extract and 1%-2% w/w Piper nigrum extract to said human in need thereof to effectively treat the vitiligo in the human in need thereof, wherein said administration is topically to the skin of the human in a form selected from the group consisting of cream, lotion, ointment, gel and emulsion.

* * * * *